United States Patent
Hanko et al.

(10) Patent No.: US 10,705,044 B2
(45) Date of Patent: Jul. 7, 2020

(54) INLINE SENSOR ARRANGEMENT AND METHOD FOR COMMISSIONING SAME

(71) Applicant: Endress+Hauser Conducta GmbH+Co. KG, Gerlingen (DE)

(72) Inventors: Michael Hanko, Dresden (DE); Angela Eubisch, Nossen (DE); Anne Heymann, Seelitz ot Spernsdorf (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 428 days.

(21) Appl. No.: 15/386,015

(22) Filed: Dec. 21, 2016

(65) Prior Publication Data

US 2017/0176372 A1    Jun. 22, 2017

(30) Foreign Application Priority Data

Dec. 21, 2015   (DE) .................... 10 2015 122 446
Dec. 16, 2016   (DE) .................... 10 2016 124 647

(51) Int. Cl.
*A61L 2/04* (2006.01)
*G01N 27/327* (2006.01)
(Continued)

(52) U.S. Cl.
CPC ............ *G01N 27/3272* (2013.01); *A61L 2/04* (2013.01); *C12Q 1/006* (2013.01); *C12Y 101/03004* (2013.01); *G01N 33/54366* (2013.01)

(58) Field of Classification Search
CPC ...................................................... A61L 2/04
See application file for complete search history.

(56) References Cited

U.S. PATENT DOCUMENTS 5,536,469 A * 7/1996 Jonsson ............. A61M 1/287
                                                          206/568
6,344,073 B1 * 2/2002 Kurosawa ............ B01D 53/28
                                                          55/524
(Continued)

FOREIGN PATENT DOCUMENTS

CN    102103113 A    6/2011
CN    102200534 A    9/2011
(Continued)

OTHER PUBLICATIONS

Guideline for Disinfection and Sterilization in Healthcare Facilities, Centers for Disease Control, 2008 (Year: 2008).*

(Continued)

*Primary Examiner* — Donald R Spamer
(74) *Attorney, Agent, or Firm* — Kelly J. Smith; PatServe

(57) ABSTRACT

The present disclosure includes an inline sensor arrangement and a method for bringing an inline sensor arrangement into service, where the inline sensor arrangement includes a sensor embodied to produce and to output a measurement signal correlated with the measured variable, and where the sensor has at least one sterile sensor element for contact with the measured medium and at least one housing, which surrounds the sensor element and encloses the sensor element in a chamber sealed from an environment of the housing. The method includes performing a heat sterilization of at least one part of the inline sensor arrangement comprising a housing exterior of the housing, opening the housing after terminating the heat sterilization, and bringing the sensor element into contact with the measured medium.

22 Claims, 2 Drawing Sheets

(51) Int. Cl.
    *G01N 33/543*     (2006.01)
    *C12Q 1/00*     (2006.01)

(56) References Cited

U.S. PATENT DOCUMENTS

| | | | |
|---|---|---|---|
| 6,379,613 B1 | 4/2002 | Stempf | |
| 2007/0041864 A1* | 2/2007 | Forsyth | A61L 2/04 422/1 |
| 2009/0105684 A1* | 4/2009 | Balteau | A61J 1/1475 604/415 |
| 2011/0107857 A1* | 5/2011 | Pfauch | G01N 27/283 73/866.5 |
| 2012/0091326 A1 | 4/2012 | Baumfalk et al. | |
| 2015/0344161 A1 | 12/2015 | Selker et al. | |

FOREIGN PATENT DOCUMENTS

| | | |
|---|---|---|
| CN | 103110969 A | 5/2013 |
| DE | 0154192 | 3/1982 |
| EP | 2065701 A2 | 6/2009 |
| WO | 2010017519 A1 | 2/2010 |

OTHER PUBLICATIONS

Moussy et al. in Vitro and In vivo Performance and Lifetime of Perfluorinated Ionomer-Coated Glucose Sensors after High Temperature Curing. Analytical Chemistry vol. 66, No. 22, Nov. 15, 1994 (Year: 1994).*

* cited by examiner

INLINE SENSOR ARRANGEMENT AND METHOD FOR COMMISSIONING SAME

CROSS-REFERENCE TO RELATED APPLICATIONS

The present application is related to and claims the priority benefit of German Patent Application Nos. 10 2015 122 446.1, filed on Dec. 21, 2015, and 10 2016 124 647.1, filed on Dec. 16, 2016, the entire contents of which are incorporated herein by reference.

TECHNICAL FIELD

The present disclosure relates to a method for bringing an inline sensor arrangement into service for registering measured values of a measured variable representing an analyte content of a measured medium.

BACKGROUND

For determining the composition of measured media, especially of liquids, such as, for example, pure liquids, liquid mixtures, emulsions or suspensions, various analytical measuring devices are applied in process measurements technology and in analytical measurements technology. An analytical measuring device includes, in general, a sensor, which is embodied to produce an electrical measurement signal dependent on at least one analytical measured variable of the measured medium, as well as an evaluating electronics, which ascertains from the measurement signal a measured value representing the current value of the at least one analytical measured variable in the measured medium. The analytical measured variable can be, for example, a concentration or activity of an analyte or a parameter dependent on a concentration or activity of at least one analyte in the measured medium. The terminology, analyte, means a substance contained, especially dissolved, in the measured medium and whose concentration in the measured medium is to be ascertained, and/or monitored, by means of the sensor. The evaluating electronics can be integrated at least partially in a measurement transmitter arranged directly at the measuring point in a housing with display and input means. At least a part of the evaluating electronics can also be arranged together with the sensor in a shared housing.

Such analytical measuring devices are applied in various fields, e.g., for monitoring and control of processes in pharmaceutical, chemical, biotechnological or biochemical production, however, also in processes for water treatment or waste water cleaning, as well as in environmental analytics. To the extent that an analytical measuring device is applied in a process, the measured medium is, as a rule, contained in a process container. Such a process container can be, e.g., a pipeline of a process installation or a reaction container, for example, a fermenter.

Sensors integrated into the wall of a process container for monitoring a measured variable of a measured medium contained in the process container are referred to as inline sensors. An inline sensor registers the measured variable directly in the measured medium to be monitored. Thus, inline sensors require no removal and pretreating of a sample from the process for determining the value of an analytical measured variable. Various adapters and assemblies, especially immersion or retractable assemblies, are known for integrating a sensor into a process wall. An arrangement, which includes an inline sensor integrated into the wall of a process container and, in given cases, an evaluating electronics connected with the inline sensor, but spaced therefrom, is referred to as an inline sensor arrangement. The inline sensor can be secured in the wall by means of a suitable adapter.

In the case of processes having to be performed under sterile, respectively aseptic, conditions, for example, processes in biotechnology, pharmacy or food technology, all parts of the process installation, especially all process containers and also sensors integrated therein, coming in contact with the process media, are, as a rule, sterilized, for example, thermally by heat, before beginning the process or between individual process steps. The heat sterilization can occur by dry heat (usually with hot air between 160° C. and 180° C. as sterilization medium) or by superheated steam as sterilization medium under increased pressure, for example, by autoclaving in a pressure vessel, i.e., so-called autoclaves. Typical, for example, are superheated steam sterilization processes, in which temperatures of at least 120° C. or more can occur. If the heat sterilization is performed in an autoclave, the process contacting parts of the process installation are (in given cases, already connected with one another) placed in the autoclave and sterilized there. The sterilized parts are then removed from the autoclave and placed in operation. Alternatively, a process installation can be sterilized by means of a so-called "sterilization in place" (SIP) method, in the case of which the process container and the inline sensor arrangements integrated therein are sterilized with superheated steam, which is introduced into the process container for a predetermined length of time. Inline sensor arrangements must, consequently, be able, without loss of functionality, to withstand the conditions, such as high temperatures and increased pressures arising in such case.

In bio-process measurement technology, for example, for monitoring and/or control of biotechnological processes, sensors are also applied, which have biological detection elements, e.g., elements, which in given cases as receptors, bind the analyte selectively and specifically. Biological detection elements can be proteins such as enzymes or antibodies, DNA/RNA fragments, cell organelles or entire cells and microorganisms. Such sensors are referred to as biosensors. After a typical superheated steam sterilization process, the receptors, such as biological detection elements of such biosensors, have, as a rule, greatly decreased activity. Most often, they are irreversibly denatured, i.e., no longer have their native 3-D structure (conformation). Such biosensors can, consequently, fundamentally not be simply inserted as inline sensors into the wall of a process container and then be sterilized along with the container by means of an established SIP process.

Many sensors with biological detection elements, e.g., those, which result from mesophilic organisms, which live in the temperature range of about 20-45° C., cannot be exposed to increased temperatures under SIP conditions, for example, above 80° C., without losing their functionality.

Described in the literature are sterilizable biosensors based on amperometric, enzyme sensors. M. Phelps, *Development of a regenerable glucose biosensor sample for bioprocess monitoring*, Master's Thesis, University of British Columbia, 1993, provides an overview of the literature of such sensors. Strategies described therein for assuring sterilizability of such biosensors while retaining their functionality comprise the bringing of the temperature sensitive receptors, arranged on a support, for example, comprising a working electrode, only after the sterilization process, into a reaction space within a sensor housing, which is closed off from the process container by a membrane permeable for the respective analyte. The membrane represents, in this case, the item that is sterilizable. In such case, the receptors can be present immobilized on the subsequently introduced working electrode or in a solution accommodated in the reaction space. During introduction of the receptors, the sterilizable item must not be damaged and this makes the handling of such inline sensor arrangements difficult.

Disadvantageous in the case of these inline sensor arrangements known from the literature is, besides the difficult handling, also that a fluctuating measuring performance of the biosensors can be observed. A reason for this is that the amount of the subsequently provided receptors is poorly reproducible. The previously known inline sensor arrangements, which comprise biosensors, are not practical, especially not as regards applications for monitoring industrial processes.

Known in the field of single-use technology frequently used for bio-processes are adapters or connectors, which enable the introduction of earlier sterilized sensors, e.g., earlier sterilized by means of gamma radiation, into a likewise earlier sterilized, single-use bioreactor (single-use fermenter). These connectors are, however, frequently not accepted, or not applicable, for use in a conventional process installation process container used multiple times for a plurality of process batches and regularly cleaned and sterilized according to one of the above described SIP sterilization methods.

The PALL Corporation of Port Washington, USA, offers, for example, connectors under the designation "Kleenpak II Sterile Connectors", which serve for the introduction of liquids or probes, including sensors, into a single-use process container. These connectors are composed of two elements connectable with one another, wherein the two elements are sealed in their connection region in the non-connected state, in each case, with a withdrawable strip. The withdrawable strips are composed of aluminum foil with a polyester coating. For introducing a probe into the bioprocess, the first element of the connector can be connected with the process container and be sterilized with such, while the second element containing the probe can be sterilized with gamma radiation or autoclaving. For introducing the probe, the two connector elements are first connected loosely with one another, thereafter the withdrawable strips are removed by lateral withdrawal, then the two elements sealedly connected with one another and, finally, the probe is shifted by the first element of the connector into the process container.

An essential disadvantage of these connectors is that the connection between the two elements does not occur aseptically with sufficient assurance, since the two outer surfaces of the withdrawable strips of the elements are not sterile, or sterilizable, and, thus, in the case of withdrawal of these strips a risk of contamination remains. Furthermore, the risk of contamination is increased by the fact that directly after the withdrawal of the withdrawable strip the two elements are not sealedly connected with one another, whereby a contamination by the non-sterile environment cannot be excluded.

These connectors are also not designed for multiply usable, stainless steel, process containers sterilizable with SIP methods.

BRIEF SUMMARY

It is, thus, an object of the present disclosure to provide an inline sensor arrangement and a method for bringing such into service, which overcome the above-described disadvantages. Preferably, the inline sensor arrangement should be universally applicable also in multi-use, cleanable and sterilizable, process containers, and permit the secure aseptic introduction of a sensor element of the inline sensor arrangement into a process container for measuring the measured variable in a medium contained in the process container. Preferably, the inline sensor arrangement should be suitable for introducing a biosensor with biological detection elements, which cannot withstand hot steam sterilization, into a process container sterilized at high temperatures.

This object is achieved by a method for bringing an inline sensor arrangement into service as defined in claim 1, an inline sensor arrangement as defined in claim 14 and a method for manufacture of an inline sensor arrangement as defined in claim 30. Advantageous embodiments are set forth in the dependent claims.

The method of the present disclosure is provided for bringing an inline sensor arrangement into service for registering measured values of a measured variable representing an analyte content of a measured medium, wherein the inline sensor arrangement includes a sensor, which is embodied to produce and to output a measurement signal correlated with the measured variable, wherein the sensor has at least one sterile sensor element provided for contact with the measured medium and at least one housing, which surrounds the sensor element and encloses the sensor element in a chamber sealed from an environment of the housing, wherein the method comprises steps as follows: performing a heat sterilization of at least one part of the inline sensor arrangement comprising a housing exterior of the housing; opening the housing after terminating the heat sterilization; and bringing the sensor element into contact with the measured medium.

The method permits the aseptic introduction of heat instable sensors into a process container, which was heat sterilized previously, while maintaining the functionality of the sensors. This is possible via application of the following described inline sensor arrangement, which includes a likewise sterile sensor element located in the interior of a sealed, sterile chamber, respectively enables the sterilization of the interior of the chamber including the sensor element, which protects the sensor element located in the sealed chamber against damage by a heat sterilization of the inline sensor arrangement externally, e.g., while the inline sensor arrangement is connected sealedly with the process container, and which enables the aseptic bringing of the sensor element into contact with a medium contained in the process container, in that the chamber is opened to the interior of the process container in the sterilized region of the housing exterior.

The part of the inline sensor arrangement subjected to a heat sterilization is, for example, the entire region of the inline sensor arrangement standing in contact, or to be brought in contact, with the interior of a process container to be kept sterile, especially the entire region of the housing exterior of the housing standing in contact with the interior of the process container to be kept sterile. Since the housing exterior, especially a region of the housing exterior, which is to be brought in contact, or is in contact, with the interior of the process container to be kept sterile, is heat sterilized, the sterile sensor element arranged in the chamber can be brought, by opening the housing in this region, safely and aseptically into contact with the interior of the process container and, in given cases, even be brought into the interior. Since the analyte sensitive (i.e., embodied for registering a measured variable correlating with the analyte content) sensor element is sealedly enclosed in the chamber during the heat sterilization of the housing exterior, it is at least protected during the heat sterilization from a sterilization medium, e.g., superheated steam, which contacts the housing exterior during the heat sterilization. It has been found that biological detection elements of the above described sensors installed in bio-process measurement technology, indeed, can lose a large part of their functionality in the case of high humidity and high temperatures, such as occur in a hot steam sterilization, but they essentially retain their functionality in the case of lesser humidity, even at the temperatures of at least 110° C. reigning in a heat sterilization. Thus, just the sealed enclosing of the sensor element in the chamber can serve for retaining the functionality of the sensor element, in spite of high temperatures in the heat sterilization of the housing exterior, so that the sensor element then introduced aseptically into the process container is functionally capable.

The sensor element can be arranged on a sensor element support, wherein the housing surrounds besides the sensor element at least one section of the sensor element support, so that at least this section is arranged within the chamber formed in the housing.

The measurement signal can be an electrical signal or an optical signal, which represents a measured value or a time sequence of measured values of the measured variable.

For bringing the inline sensor arrangement into service, it can be integrated into a wall of a process container before the performing of the heat sterilization, and the heat sterilization of the inline sensor arrangement can be performed together with a heat sterilization of the process container in a single method step, wherein the now sterilized housing standing in contact with the interior of the process container is opened to the process container after termination of the heat sterilization. This can occur, for example, in the context of an SIP method. The integration of the inline sensor arrangement into the wall of the process container can occur by means of an assembly, e.g. a retractable assembly, or a process connection, which is connected sealedly, especially fluid-tightly, i.e. gas and/or liquid tightly, with the inline sensor arrangement. The connection is, in such case, preferably effected in such a manner that the process container is sealed fluid-tightly from the environment of the process container. This is preferably accomplished by means of one or more hygienic sealing elements, which are embodied in such a manner that their surfaces in contact with the interior of the process container are sterilizable by means of an SIP method. This sealing element can be e.g. a suitable, hygienic, shaped seal, such as are known basically from the state of the art for assemblies, including retractable assemblies, for use in hygienic applications.

The performing of the heat sterilization can also occur in an autoclave. In such case, the inline sensor arrangement can already be connected with the process container and the two can be placed in the autoclave and sterilized therein.

For aseptic opening of the housing and contacting of the sensor element with the measured medium, the region of the housing standing in contact with the interior of the process container can be hygienically embodied, especially edge, burr and gap free.

In order to assure that the sensor is not exposed to too much humidity during the heat sterilization, the housing of the inline sensor arrangement can be embodied in such a manner and the chamber sealed from the environment in such a manner that during the heat sterilization of the housing externally at a temperature of at least 110° C. the relative humidity reigning within the housing does not exceed a value of 77%, preferably 23%, further preferably 3%, yet further preferably 1%. During the heat sterilization, the relative humidity within the chamber enclosing the sensor element can be monitored by means of a humidity sensor of the inline sensor arrangement. The humidity sensor can be a component of the inline sensor arrangement.

The housing can comprise a wall formed from one or more housing components enclosing the chamber gastightly and forming a barrier against the diffusion of steam into the chamber. Advantageously, an average water vapor permeability of the housing wall, i.e. an average value of the water vapor permeability of the components forming the wall, amounts, in the case of a temperature of 110° C., a pressure difference reigning between the chamber and the environment of the wall of less than 5 bar and a difference of the relative humidities reigning in the chamber and in the environment of the wall of greater than 67%, to less than 420 grams of water per square meter and day ($g/m^2 \cdot d$), preferably less than 125 $g/m^2 \cdot d$, further preferably less than 15 $g/m^2 \cdot d$, yet further preferably less than 6 $g/m^2 \cdot d$.

The wall, respectively the housing components forming the wall, can be formed of a material, through which steam cannot diffuse or diffuses only to a small degree, e.g. materials such as glass, plastic or metal. An option is also the application of a composite material, e.g. a multi-ply, composite material. A multi-ply composite material suitable for such purpose can comprise, for example, at least one plastic ply and a metal ply or a metallized layer. Also, multi-ply materials of different plastics, e.g. bonded foils, are applicable, e.g. PET-PE, PET-PVCD/PE or PE-EVOH-PE or plastic foils bonded with metal layers such as e.g. a composite of PET-aluminum-PE or aluminum-PET-aluminum. Additionally, one or multi-ply plastics coated with aluminum oxide or silicon oxide can be used, e.g. PET-SiOx/PE.

The sensor element can have at least one biological detection element for the analyte. Biological detection elements can be proteins such as enzymes or antibodies, DNA/RNA fragments, cell organelles or entire cells and microorganisms. The biological detection element binds the analyte, for example, specifically or enters into a chemical reaction with the analyte. For example, the sensor can be an amperometric, enzyme sensor. For example, the sensor element can have as detection element an enzyme, which is lyophilizable while maintaining at least 10% of its activity. The sensor can be an enzyme-based, glucose sensor, e.g. with glucose oxidase as detection element. An example here is a glucose oxidase comprising, glucose sensor manufactured and sold with the designation B.LV5, B.IV4 by Jobst Technologies GmbH, Freiburg, Germany. These amperometric, enzyme based sensors can also comprise lactate oxidase as detection element for lactate sensors, glutamate oxidase for glutamate sensors, and glutaminase for glutamine sensors.

Additionally or alternatively for protection from too high humidity, it can be advantageous to decouple the sensor element at least at times, especially during the performing of the heat sterilization, thermally from the environment of the housing, i.e. the environment of a housing exterior of the housing. The sensor element can be decoupled, especially during the above described method for bringing in service, until after termination of the heat sterilization, thermally from the environment of the housing. Advantageously, the sensor element is, in such case, decoupled thermally in such a manner from the environment of a housing exterior of the housing that during the heat sterilization of the inline sensor arrangement the temperature of the sensor element rises to less than 80° C., preferably less than 50° C., further preferably less than 35° C. This can serve supplementally or alternatively for assuring a small relative humidity within the chamber to prevent a degrading of the measuring characteristics of the sensor element, especially to the extent that it includes biological detection elements.

For the purpose of the at least temporary thermal decoupling of the sensor element from the environment of the housing, the sensor element can, for example, during a heat sterilization, be arranged spaced from the volume of the process container to be sterilized and from the parts contacted by the sterilization medium. For example, the process container can have a connection, which surrounds a connector space communicating with the process container, and which is connected before the performing of the heat sterilization with a process connection of the inline sensor arrangement complementary to the connection. The process connection is, in such case, connected in such a manner with the housing of the inline sensor arrangement that the sensor element is arranged on a side outside of the connection space and facing away from the process container, when the process connection and the connection of the process container are connected with one another. For example, an end face of the housing of the inline sensor arrangement can close the connector space, when the connection of the process container is connected with the process connection of the inline sensor arrangement. In this case, only the end face of the housing comes in contact with the sterilization medium and is heated by this, while the sensor element behind the end face is arranged separated from the end face and, thus, is exposed to lesser temperatures. In this way, a thermal decoupling of the sensor element from the interior of the process container, which can be exposed to a heat sterilization, can be achieved.

Advantageously, the inline sensor arrangement can in the case of its bringing in service be cooled before the heat sterilization, preferably to less than 8° C., further preferably to less than −13° C., further preferably to less than −20° C. During the heat sterilization, the temperature of the at least one sensor element can be monitored by at least one temperature detector/sensor of the inline sensor arrangement.

An inline sensor arrangement for registering measured values of a measured variable representing an analyte content of a measured medium, especially an inline sensor arrangement suitable for performing the above described method, includes a sensor, which is embodied to produce and to output a measurement signal correlated with the measured variable, wherein the sensor has at least one sterile sensor element provided for contact with the measured medium, and, surrounding the at least one sensor element, a housing, which encloses the sensor element in a chamber sealed from an environment of the housing.

The inline sensor arrangement is, as already described above, especially embodied for introducing a sensor element, especially a heat instable sensor element, aseptically into a process container, which was earlier heat sterilized. The inline sensor arrangement can be integrated for this into a wall of a process container, for example, by means of an assembly, e.g. a retractable assembly, or a container connection. By enclosing the sensor element in a housing chamber sealed from the environment, the likewise sterile sensor element can, during a heat sterilization of the housing exterior to be brought in contact or in contact with the interior of the process container, which heat sterilization can occur e.g. together with the heat sterilization of the interior of the process container, be protected from the sterilization medium, and so the functionality of the sensor element essentially retained. Then, the sensor element, such as described above, be brought, by opening of the housing, aseptically into contact with the interior of the process container, respectively a measured medium located therein, in a region located within the process container and, especially, heat sterilized together with the process container.

In order to assure that the sensor is not exposed during the external heat sterilization of the housing to too much humidity, the housing of the inline sensor arrangement can be embodied in such a manner and the chamber sealed from the environment in such a manner that during the heat sterilization of the housing externally at a temperature of 110° C. the relative humidity reigning within the housing does not exceed a value of 77%, preferably 23%, further preferably 3%, yet further preferably 1%.

The inline sensor arrangement can have at least one humidity sensor, which is embodied to register measured values representing a relative humidity reigning within the chamber. The inline sensor arrangement can further be embodied to register by means of the humidity sensor, at least during the performing of a heat sterilization of the inline sensor arrangement, measured values representing the relative humidity reigning within the chamber as a function of time.

The housing can comprise a wall formed by one or more housing components for sealed enclosure of the chamber and forming a barrier against the diffusion of steam into the chamber. Advantageously, an average water vapor permeability of the wall, i.e. an average value of the water vapor permeability of the components forming the wall, at a temperature of 110° C., a pressure difference reigning between the chamber and the environment of the housing wall of less than 5 bar and a difference of the relative humidities reigning in the chamber and in the environment of the wall of greater than 67%, amounts to less than 420 g/m²·d, preferably less than 125 g/m²·d, further preferably less than 15 c, most further preferably less than 6 g/m²·d.

In order to keep the humidity in the chamber low, the chamber can contain a drying means, for example, silica gel or zeolite.

It is also an option that the inline sensor arrangement further comprises at least one opening into the chamber for supplying a water-free or low humidity fluid, especially pure nitrogen or air with a water content of less than 50 ppmv (parts per million by volume) $H_2O$, further preferably less than 5 ppmv $H_2O$. The supply line can include a sterile filter arranged in the flow path of the fluid. The supply line can be connected with a reservoir, which contains the fluid, especially nitrogen or air. Furthermore, a drain line for the fluid can communicate with the chamber. Preferably, the drain line likewise includes a sterile filter. The supply and drain lines are preferably arranged outside of the process container.

The at least one sensor element can supplementally or alternatively to the above described measures for assuring a small relative humidity within the chamber at least at times be thermally decoupled or thermally decoupleable from the environment of the housing exterior of the housing. For example, it can be thermally decoupled from the housing exterior of the housing in such a manner that during the action of a medium having a temperature of 110° C. on at least one portion of the housing exterior for a time of 15 minutes (min) the temperature of the sensor element rises from a starting temperature of the sensor element of 25° C. at beginning of this period of time by less than 55° C., preferably less than 35° C., further preferably less than 10° C. Such conditions occur, for example, in the case of a heat sterilization of the housing exterior, e.g. in the context of an SIP method performed in a process container, in which the inline sensor arrangement is integrated. In this case, the medium can be, for example, dry hot air or superheated steam.

The inline sensor arrangement can be provided with at least one temperature detector/sensor, which is embodied to ascertain the temperature of the at least one sensor element as a function of time, especially during a heat sterilization of at least one portion of the housing exterior.

The thermal decoupling can be achieved, for example, by a thermal isolation or thermal insulation of the sensor element from the housing exterior, whereby the amount of heat transferred per unit time between housing exterior and sensor element is reduced in comparison to an embodiment of the inline sensor arrangement, in the case of which no isolation or insulating of the sensor element from the housing exterior is provided, so that the temperature change of the sensor element is correspondingly prevented or slowed.

Advantageously, the thermal decoupling is achieved by arranging a heat-insulating material between the sensor element and the housing exterior and/or by providing at least at times a pressure of less than 100 millibar (mbar) in the housing. The terminology, heat-insulating material, means here especially a homogeneous material of low thermal conductivity or an at least two-phase material with gas filled hollow spaces, especially a microporous fill material. The material of low thermal conductivity can advantageously have a thermal conductivity of ≤0.5 Watts per meter-Kelvin (W/m·K). The housing advantageously forms a chamber surrounding the sensor element gas tightly.

Alternatively or supplementally, the inline sensor arrangement can comprise means for active and/or passive cooling of the sensor element, whereby the amount of heat transferred per unit time between housing exterior and sensor element is at least partially drained from the sensor element, so that temperature change of the sensor element is prevented or slowed. These means can comprise, for example, a gas cooling, a cooling with cooling liquid, a Peltier cooling, cooling fins or some other heat sink.

In order to enable a thermal decoupling of the sensor element from the housing exterior by lessening the pressure within the housing, especially to a pressure of less than 100 mbar, the housing can have a gas outlet communicating with the chamber for evacuation of the chamber. The gas outlet is gas tightly closable. The housing forms in this embodiment in the case of gas tightly closed gas outlet a chamber gas tightly surrounding the sensor element. The gas outlet can advantageously include a sterile filter. Advantageously, the gas outlet is arranged outside of the process container, when the sensor arrangement is integrated in the process container.

The gas outlet can in a further development of this embodiment end in a sealable connector, especially a releasably sealable connector, which is connectable to a vacuum pump. The housing, respectively the chamber formed therewith, can, consequently, be evacuated, for example, directly before performing the sterilization of the process container, in which the inline sensor arrangement is integrated. Alternatively, it is also possible to integrate in a wall of the process container an inline sensor arrangement, whose housing has already been evacuated and then sterilized with included sensor element using a suitable method. The terminology, evacuate, means here especially the reducing of the pressure reigning in the housing to a value of <100 mbar. It is advantageous to perform the sterilization of the housing, with included sensor element, in the end packaging with gamma radiation. For better assuring that a negative pressure reigns in the housing for thermal decoupling from the environment of the housing exterior of the at least one sensor element, the housing with included sensor element can in the case of the end packaging be vacuum packed with an evacuating device.

In an additional embodiment, the inline sensor arrangement includes a cooler serving for at least temporary thermal decoupling of the sensor element from the environment of the housing exterior for at least temporary cooling of at least one part of the inline sensor arrangement.

The cooler can be purely passive in nature, for example, it can comprise a heat sink standing in heat conducting contact with the sensor element.

Additionally or alternatively, the cooler can for active cooling of the sensor element comprise at least one thermoelectric transducer, e.g. a Peltier element. Such is advantageously so arranged that it cools a sensitive surface of the sensor element intended for contact with the measured medium for performing measurements.

In an additional embodiment, the cooler can comprise a fluid cooling. This can advantageously have in a sensor element support, on which the sensor element is arranged, and/or in the housing wall of the housing, a duct structure capable of being flowed through by fluid.

In order to improve the thermal decoupling, it is advantageous that the housing or at least one or a number of components forming the housing be formed of a thermally insulating plastic, especially PEEK, having a thermal conductivity of ≤0.5 W/m·K.

For contacting the sensor element, or a sensitive surface of the sensor element, with a measured medium located outside of the housing, the housing can have a wall region, which is embodied to bring the sensor element in contact with the environment of the housing. For example, the wall region can be embodied to be opened, in order to establish a connection between the sensor element, respectively the chamber containing the sensor element, and the environment of the housing. This wall region is arranged in a region of the housing, which includes a housing exterior of the housing within contact or standing in contact with the interior of the process container.

The sensor element and the wall region can be movable relative to one another in such a manner that the sensor element can be shifted out from the housing.

In an embodiment of the inline sensor arrangement, in the case of which the sensor element is arranged on a sensor element support, the sensor element support can be mounted movably relative to the housing, so that a relative movement of the sensor element support relative to the housing effects a transport of the sensor element out from the opened housing.

For example, the housing, especially the chamber containing the sensor element, can have a wall region, which is embodied as a weak point. For establishing a contact between the sensor element and the housing environment, the sensor element support can have a point or edge, which is embodied in such a manner that in the case of a movement of the sensor element support relative to the wall region leading to a contact of the end section of the sensor element support with the wall region, it pokes through or cuts open the wall region. This wall region can be embodied, for example, as an end wall of the housing standing in contact with the interior of the process container and/or facing the process container, and formed, for example, by a membrane or film.

Alternatively, the housing can include a cap, a lid or a lock arrangement, which is movable relative to the housing, so that the housing is opened by a movement of the cap, the lid or the lock arrangement relative to an additional housing part, in such a manner that a contact between the sensor element and the environment of the housing is produced. When the inline sensor arrangement is integrated in the process container, the cap, the lid or the lock arrangement stands in contact with the interior of the process container and can in the case of a heat sterilization be sterilized together with such, so that an actuating of the lock arrangement cannot lead to the fact that the interior of the process container comes in contact with unsterile parts or with an unsterile environment.

As already described above in connection with the method for bringing an inline sensor arrangement into service, the sensor element can have biological detection elements. A biological detection element can be, for example, a lyophilizable enzyme maintaining at least 10% of its activity. For example, the sensor element can comprise glucose oxidase. The sensor can be e.g. an amperometric, enzyme based sensor, especially an enzyme based sensor comprising glucose oxidase.

The housing can be formed of glass and/or have at least one metal ply and/or a ply of synthetic material and/or comprise a plurality of solid particles, especially metal particles, especially such acting as diffusion barriers for steam. The metal particles can, for example, be embedded in the form of spheres or platelets in a plastic to form a wall or a seal or a connecting location or a potting compound of the housing.

The sensor element can comprise one or more electrodes, wherein lines contacting the electrodes extend through a channel formed within a sensor element support, on which the sensor element is arranged.

The sensor can further include a measurement circuit, which is connected with the lines and which is embodied to register an electrical signal correlating with the measured variable. In the case, in which the sensor is embodied as an amperometric sensor, the measurement circuit serves to apply a voltage between at least two electrodes of the sensor and to register electrical current flowing in such case and to output such or an electrical signal derived therefrom as a measurement signal. The inline sensor arrangement can include an evaluation circuit, which is embodied to ascertain from the electrical signals output by the measurement circuit measured values of the measured variable in the units of the measured variable and to output such via an interface to a superordinated unit or via a display system, e.g. a display.

The present disclosure relates also to a method for manufacturing an inline sensor arrangement according to one of the above described embodiments. The method includes manufacturing an inline sensor arrangement with a sensor, which is embodied to produce and to output a measurement signal correlated with the measured variable, wherein the sensor has at least one sensor element provided for contact with the measured medium, and with a housing surrounding the sensor element and at least one section of the sensor element support and enclosing the sensor element in a chamber sealed from an environment of the housing; and sterilizing the at least one sensor element of the inline sensor arrangement in the chamber by means of beta or gamma radiation.

The manufacture of the inline sensor arrangement can further comprise the sealed closing of the chamber, wherein a relative humidity present in the chamber after the closing is so selected that during a heat sterilization of the housing externally at a temperature of 110° C. for a duration of 15 min the relative humidity reigning within the chamber does not exceed a value of 77%, preferably 23%, further preferably 3%, most further preferably 1%.

The method can further comprise the thermal decoupling of the at least one sensor element from the environment of a housing exterior of the housing.

BRIEF DESCRIPTION OF THE DRAWINGS

The present disclosure will now be explained in greater detail based on the examples of embodiments illustrated in the drawing, the figures of which show as follows.

DETAILED DESCRIPTION

Figure 1:
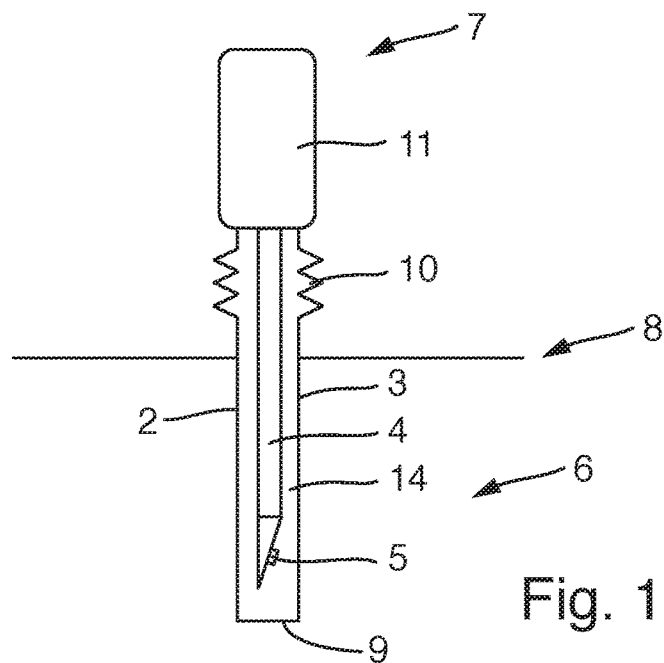
FIG. 1 shows a schematic representation of a first example of an embodiment of an inline sensor arrangement integrated into the wall of a process container.

FIG. 1 shows schematically an inline sensor arrangement 7, which is integrated into the wall of a process container 8, e.g. a pipeline or a fermenter. Performed in the process container 8 is a biotechnological process to be protected against contamination. For integrating the inline sensor arrangement 7 into the process container 8, the inline sensor arrangement 7 can have a process connection (not shown in FIG. 1), which is connected fluid-tightly with a connection of the process container 8 complementary to the process connection. Alternatively, the inline sensor arrangement 7 can be arranged in an assembly, e.g. a retractable assembly, which is secured fluid-tightly to a connection of the process container 8.

The inline sensor arrangement 7 includes a sensor, which includes an analyte sensitive, sensor element 5 and a measurement circuit (not shown) connected with the sensor element 5. For measuring an analytical measured variable of a measured medium, the analyte sensitive, sensor element 5 must be brought in contact with the medium. The sensor element 5 can have, for example, one or more electrodes, which are modified with biological detection elements. The detection elements can comprise, for example, compounds immobilized on the electrode surface and specifically binding the analyte. Specifically binding compounds include e.g. enzymes or proteins. The sensor element 5 is arranged on a sensor element support 4. The sensor element support 4 is rod-shaped in the example shown here. Formed within the rod-shaped sensor element support 4 can be a hollow space, e.g. a channel extending in the axial direction, through which lines (not shown) electrically contacting the sensor element 5 are led.

On an end facing away from the process, the inline sensor arrangement 7 includes an electronics housing 11, in which the measurement circuit serving for registering measured values is arranged. The measurement circuit is electrically conductively connected with the lines led through the sensor element support 4 and embodied to produce electrical measurement signals correlating with the measured variable to be registered. In the example shown here, the sensor of the inline sensor arrangement 7 is embodied as an amperometric, enzyme sensor. In this case, the measurement circuit is embodied to apply or to bring about a voltage between two electrodes of the sensor element 5 and to register the electrical current flowing, in such case, through a measured medium contacting the two electrodes. The measurement circuit yields as measurement signal the registered electrical current or a value derived therefrom, especially a digital value. The measurement circuit can be connected with a superordinated, evaluating or control unit (not shown), which receives and further processes the measurement signals output from the measurement circuit. The electronics housing 11 can have for connection with the superordinated evaluating or control unit an interface, for example, an interface comprising a primary side of a plugged connection. The evaluating or control unit can be connected via a cable, which comprises the secondary side of the plugged connection, with the inline sensor arrangement 7.

The inline sensor arrangement 7 includes a supplemental housing 2, which surrounds a section of the sensor element support 4 protruding into the process container and supporting the sensor element 5. In the example shown here, the housing 2 includes a number of housing components, namely a tubular shaft 3, which is sealed on an end protruding into the process container 8 by an end wall 9, and a bellows 10 connected with the shaft 3 on the end of the shaft 3 lying opposite the wall. The end wall 9 can be formed by a metal, plastic, composite film, which is connected with the tubular shaft 3 by material bonding, e.g. by means of an adhesive or potting compound. On its end lying opposite the wall 9, the housing 2 is sealed by a potting compound (not shown) and connected with the electronics housing 11.

Housing 2 encloses the front section of the sensor element support 4 including the sensor element 5 completely in a gas-sealed chamber 14, so that no connection is present between the volume of the chamber 14 enclosed in the housing 2 and an interior 6 of the process container 8. The gas-sealed chamber 14 contains a gas, e.g. nitrogen, or a gas mixture, for example, air. The humidity present in the chamber 14 is so selected that at a temperature of 110° C. the relative humidity in the chamber amounts to less than 77%. Additionally, a desiccant, e.g. silica gel, zeolite, or the like, can be provided in the chamber, in order to reduce the relative humidity in the chamber 14 further.

Housing 2 forms a barrier to the diffusion of water, or steam, from the environment into the chamber. The average water vapor permeability of the housing 2 formed in the present example by a number of housing components of different materials amounts, at a temperature of 110° C. and a pressure difference between the environment and the chamber 14 of less than 5 bar and a difference of the relative humidities within the chamber 14 and the environment of greater than 67%, to less than 420 g/m²·d or preferably even smaller. The different materials of the components of the housing 2 are so selected that the water vapor permeability of the housing 2 lies, on average, under this value. Examples of suitable materials include PPSU, ECTFE, PEEK, PPS, PFA and PCTFE.

Examples of materials for the tubular shaft 3 include glass, metal or plastics having a correspondingly low water vapor permeability. These are, for example, metals, or water vapor impermeable plastics.

Examples of materials for a housing wall, especially for the tubular shaft 3, or the end wall 9, include, moreover, composite materials, such as e.g. multi-ply materials, which comprise at least one ply of a material forming a strong barrier against the diffusion of water from the environment. For example, the composite material can comprise a film having a ply of metal, e.g. aluminum, and/or a ply of a barrier plastic. For example, such a composite material can be a metal coated plastic. A composite material suitable for the shaft 3 or the end wall 9 can comprise, moreover, instead of a continuous ply of the material with high barrier action also a plurality of particles of such a barrier material embedded in a base material, e.g. a plastic. The embedded particles can be metal particles, for example.

The potting compound, adhesive or seal material sealing chamber 14 can likewise be material with high barrier action. Especially, such can be formed of a barrier plastic or composite material, e.g. a polymer comprising solid particles.

An option is that a potting compound or a seal, forming, as compared with the shaft 3 and the end wall 9, only a small part of the wall bounding the chamber 14, is formed of a conventional potting compound or sealing material used for liquid analysis sensors. If these materials have a low barrier action for steam, this can be overcome by selecting for the shaft 3 or the wall 9 a material with very smaller water vapor permeability, so that the water vapor permeability of all components of the housing enclosing the chamber 14 remains, on average, under the above mentioned limit value.

The water vapor permeability of a material is given in the units, g/m²·d. This is gravimetrically determined based, for example, on DIN 53122-1/DIN 53122-A, wherein a test container filled with a desiccant is sealed by a sample of the material being tested and exposed to a defined test climate. The amount of water passing through the sample is determined by weighing. Related standards are ISO 2528:1995 and ASTM E-96.

Before performing a biotechnological process to be performed under sterile, or aseptic, conditions in the process container 8, the inline sensor arrangement 7 can be sealedly connected integrated in the housing wall of the process container 8. The chamber 14 as well as the sensor support 4 and the sensor element 5 are, at this point in time, already sterile. A sterilizing of the chamber 14 and the therein arranged elements can occur, for example, by means of irradiation with gamma radiation. The sterilizing can advantageously be performed by the manufacturer during manufacture of the sensor element 5 and/or the inline sensor arrangement 7.

Bringing of the inline sensor arrangement 7 into service occurs in following manner. In a first step, the process container 8 together with that part of the outside of the housing 2 of the integrated inline sensor arrangement 7 in contact with the process container 8 is heat sterilized, for example, by means of hot steam sterilization. The superheated steam acts, in such case, only on that part of the outside of the housing 2, which is in contact with the interior 6 of the process container. A typical temperature versus time curve of the housing exterior exposed to the superheated steam includes a heat up phase from a starting temperature, e.g. room temperature (about 25° C.), to 140° C. over a time span of 1 hour (h), a phase, for example, of 1 h duration, during which the temperature is held at 140° C. and an adjoining cool down phase, during which the housing is cooled to room temperature during a time span of, for example, 4 h. In order to achieve a complete sterilizing, sealing elements, which seal the connection of the inline sensor arrangement 7 with the process container 8, are hygienically embodied, i.e. their surface regions in contact with the interior 6 of the process container 8 are completely accessible for and sterilizable by the sterilization medium, in the present example, superheated steam. Also, the housing exterior of the housing 2 standing in contact with the interior 6 of the process container 8 is hygienically embodied, i.e. it has no gaps or burrs or edges, which are not completely accessible for the sterilization medium and therewith sterilizable.

After completion of the sterilization and after cooling of the process to temperatures of less than 80° C., preferably less than 60° C. or even less than 40° C., a contact between the sensor element 5, and/or the chamber 14, and the interior 6 of the process container 8 is made, in order to enable the registering of measured values in a measured medium contained in the process container 8 or flowing through the process container 8.

In the present example, the end wall 9 of the housing 2 facing the process container 8 and standing in contact with its interior 6, is embodied sufficiently thinly that it can be pierced by action of a mechanical force. The end of the sensor element support 4 with the sensor element 5 facing wall 9 has a point or edge. The sensor element support 4 is axially movably mounted, in the example shown here by means of a wall region of the housing 2 embodied in the form of a bellows 10. Here and in the following description of further examples of embodiments, the terminology "axially" is used with reference to a cylindrical symmetry axis of a sensor element support or a tubular housing shaft of the inline sensor arrangement. The bellows 10 can be compressed in such a manner that the difference between the length of the housing 2 (measured in the axial direction) in the expanded state of the bellows 10 and the length of the housing 2 in the case of maximum compressed bellows 10 is greater than the separation between the end wall 9 and the sensor element 5, wherein this separation corresponds to a distance extending in the axial direction between the wall 9 and the part of the sensor element 5 farthest removed from the wall 9. The inline sensor arrangement 7 can supplementally have locking elements (not shown in FIG. 1), which lock the bellows in the compressed state. If the bellows 10 is collapsed, the sensor element 5 pokes through the wall 9 and protrudes out of the end of the housing 2. In this way, the chamber 14 is opened to the interior 6 of the process container 8 and the sensor element 5 is brought in contact with a process medium contained in the process container 8 or flowing through same. The establishing of the contact between the sensor element 5 and the interior 6 of the process container 8 occurs, in such case, aseptically, since the sensor element 5 and the interior of the chamber 14 were sterilized before the opening. In the opening of the wall 9, there is no opportunity for contact with the unsterile environment of the process container or with unsterile parts of the inline sensor arrangement 7. In the compressed state of the bellows 10, the inline sensor arrangement 7 can serve to monitor a measured variable to be registered for the measured medium contained in the process container 8 or flowing through same.

Alternatively, the inline sensor arrangement 7 can in the case of bringing it into service be subjected together with the process container 8 to a heat sterilization in an autoclave. The sterilized process container 8 can together with the sterilized inline sensor arrangement 7 then be installed in a biotechnological plant and used for performing a biotechnological process. The aseptic introduction of the sensor element 5 into the process container 8 occurs in this embodiment in the same manner as described above. Especially, also here, contact with unsterile parts or the unsterile environment is prevented.

After completion of the biotechnological process, the sensor is disposed of, since a renewed sterilizing of the process container 8 with the inline sensor arrangement 7 is not possible in the example of an embodiment described here, in the case of which the housing 2 is irreversibly damaged in the process of bringing the in-line sensor arrangement 7 into service. If the process container 8 is to be used anew, in order to perform a new bioprocess, first, the inline sensor arrangement 7 is replaced with an unused inline sensor arrangement 7 of the same type having an intact housing 2.

If the components of the housing 2 of the inline sensor arrangement 7 enclosing the chamber 14 have, on average, a water vapor permeability of less than 420 g/m²·d, preferably less than 125 g/m²·d, further preferably less than 15 g/m²·d or even less than 6 g/m²·d, then there is so little penetration of steam into the chamber 14 during the heat sterilization, e.g. with superheated steam, that the relative humidity within the chamber 14 over the entire duration of the heat sterilization does not rise above a value of 77% or even much less, e.g. the relative humidity lies below 23% or even below 3%. The relative humidity can even remain below 1% in the case of suitable choice of material for the housing. Such values can also be achieved, when the relative humidity of the air trapped in the chamber 14 during the manufacture of the inline sensor arrangement 7 amounts at room temperature (25° C.) up to about 30%. It has been found that under these conditions, no degrading of the biological detection elements occurs, in spite of the high temperatures arising in the heat sterilization, for example, using the temperature versus time plan explained above. This was the case, for example, for sensor elements of enzyme based glucose sensors, which comprise glucose oxidase as biological detection element, for example, those manufactured and sold under the designation B.LV5, B.IV4 by Jobst Technologies GmbH, Freiburg, Germany.

The housing 2 can have an outer diameter of about 12 mm. Many standard assemblies, e.g. retractable assemblies, which are used in process measurements technology for integration of sensors into the wall of process containments, are embodied to accommodate rod-shaped sensors having an outer diameter of 12 mm. If the housing 2 has an outer diameter of 12 mm, it can be directly integrated into the wall 9 of the process container 8 by means of such conventional assemblies.

The manufacture of the inline sensor arrangement 7 can occur such that the sensor element support 4 with the sensor element 5 arranged thereon is inserted into the tubular shaft 3 already fixedly connected with the wall 9 and the bellows 10, while the housing 2 is still open on its end lying opposite to the wall 9. In an additional step, the housing 2 can then be sealed on this end by a potting compound to form the chamber 14 enclosing the sensor element support 4 and the sensor element 5, wherein at least the electrical lines contacting the sensor element 5 are led through the potting compound, in order to be connected with a measurement circuit outside of the chamber 14. The circuit board comprising the measurement circuit is arranged in the electronics housing 11, which is affixed to the housing 2.

Before sealing the chamber 14, the humidity in the chamber can be so set that the relative humidity within the chamber 14 remains at a temperature of 110° C. below the above mentioned limit values. For example, to this end, a dried gas can be enclosed in the chamber 14 and/or a desiccant placed in the chamber 14. The manufacture can, moreover, include the sterilizing of the interior of the chamber 14, including the sensor support 4 and the sensor element 5, by means of gamma radiation. Alternatively, this can be done shortly before the bringing of the inline sensor arrangement 7 into service by the operator of the plant, in which the biotech process to be monitored by means of the inline sensor arrangement 7 is performed.

Figure 2:
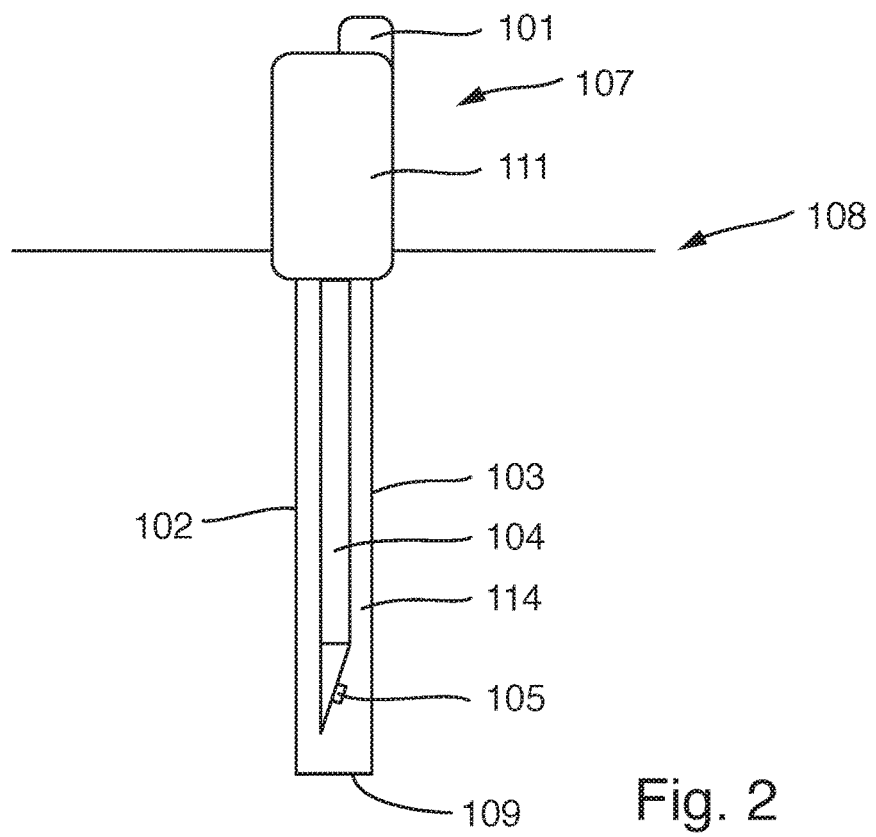
FIG. 2 shows a schematic representation of a second example of an embodiment of an inline sensor arrangement integrated into the wall of a process container.

FIG. 2 shows a schematic representation of an additional example of an embodiment of an inline sensor arrangement 107, which is integrated into the wall of a process container 108. The process container can be e.g. a pipeline or a fermenter, which is formed of a material, e.g. stainless steel, suitable for the process, for example, a biotechnological process, performed in the process container 108. The inline sensor arrangement 107 permits a thermal decoupling of a sensor element 105 with biological detection elements from components, e.g. a housing exterior, of the inline sensor arrangement 107 exposed to a heat sterilization. In this way, it can be assured that, even in the case of a sterilizing of the inline sensor arrangement 107 by means of a heat sterilization, the biological detection elements are not exposed to temperatures leading to a denaturing of the detection elements and therewith to a degrading of the functionality of the sensor element 105.

Inline sensor arrangement 107 includes a sensor, which is formed essentially by an analyte sensitive, sensor element 105 and a measurement circuit connected with the sensor element 105. Sensor element 105 is designed to be brought in contact with a measured medium contained in the process container 108 for measuring an analytical measured variable of the measured medium. It can have, for example, one or more electrodes, which are modified with biological detection elements, for example, substances, such as enzymes or proteins, specifically binding the analyte. Sensor element 105 is arranged on a rod-shaped sensor element support 104. Within the rod-shaped sensor element support 104, a hollow space can be formed, e.g. a channel extending in the axial direction, and through which lines (not shown) electrically contacting the sensor element 105 are led.

On its end facing away from the process, the inline sensor arrangement 107 includes an electronics housing 111, in which the measurement circuit serving for registering measured values is arranged. The measurement circuit is electrically conductively connected with the lines led through the sensor element support 104 and embodied to produce electrical measurement signals correlating with the measured variable to be registered. The measurement circuit can be embodied analogly, such as in the case of the measurement circuit of the example of an embodiment illustrated in FIG. 1. It can likewise be connected with a superordinated evaluating or control unit, which receives and further processes the measurement signals output by the measurement circuit. The electronics housing 111 can have an interface, for example, an interface comprising a primary side of a plugged connection, for connection with the superordinated evaluating or control unit. The evaluating or control unit can be connected via a cable with the inline sensor arrangement 107, wherein the cable includes the secondary side of the plugged connection.

Inline sensor arrangement 107 includes a supplemental housing 102, which surrounds a section of the sensor element support 104 protruding into the process container 108 and including the sensor element 105 in a chamber 114 gas tightly sealed from the environment of the inline sensor arrangement, especially from the interior of the process container 108. In the example shown here, the housing 102 includes a tubular shaft 103 and an end wall 109 closing the tubular shaft 103. On the end opposite the wall 109, the tubular shaft is closed and sealed by a potting compound. The chamber 114 enclosed in the housing 102 can contain a gas, e.g. nitrogen, or a gas mixture, for example, air.

Led through electronics housing 111 is a gas line, whose first end opens into the interior of the housing 102, more exactly into the chamber 114, and whose second end has a connector 101. The connector 101 can be secured on the electronics housing 111. Advantageously, the connector 101 can be embodied as a sterile connector. In order to lessen the pressure reigning within the housing 102, connector 101 can be connected with a vacuum pump. The evacuation of the housing 102, respectively the sinking of the pressure reigning in the housing 102 to a value of less than 100 mbar, serves for thermal decoupling of the sensor element 105 arranged on the sensor element support 104 from the outside of the housing 102, i.e. from the outer surface of the housing wall facing the environment of the housing 102, respectively from the environment of the outside of the housing 102. The inside of the housing 102, i.e. the housing inner wall facing into the chamber 114, can be reflectively coated as an additional measure for thermal decoupling.

For placing the inline sensor arrangement 107 in service, before beginning to perform a bioprocess in the process container 108, the inline sensor arrangement 107 can be integrated in the housing wall of the process container 108. The chamber 114 as well as the sensor support 104 and the sensor element 105 are, at this point in time, advantageously already sterile. Advantageously, the sensor element 105 is, at this point in time, also already thermally decoupled from the environment of the housing exterior or the outwardly directed housing wall surface. A sterilizing of the interior of the housing 102 and the therein arranged elements can be accomplished, for example, by means of irradiation with gamma radiation. The sterilizing can, same as the evacuation of the housing 102, advantageously be performed by the manufacturer as part of the manufacture of the inline sensor arrangement 107.

For thermal decoupling of the sensor element 104 from the outside of the housing 102, before or even after integration of the inline sensor arrangement 107 into the process container 108, the volume enclosed by the housing 102 can be evacuated by means of a vacuum pump connected with the connector 101, wherein a pressure of less than 100 mbar is produced in the housing 102. Then, the process container 108 can be sterilized together with the integrated inline sensor arrangement 107, for example, by means of hot steam sterilization. The superheated steam acts, in such case, only on the outside of the housing 102. The evacuation of the housing 102 effects, supplementally to the insulating properties of the housing wall, a thermal insulation of the sensor element 105 from the housing exterior. Thus, there occur in the case of a heat sterilization, in the case of which the housing exterior, i.e. the outwardly directed wall surface of the housing 102, is exposed to a sterilization medium having a temperature of at least 110° C., temperatures of <80° C., preferably <40° C., at the location of the sensor element. Such low temperatures do not degrade the activity of the biological detection elements of the sensor element 105 and therewith the functionality of the sensor or, if at all, in a measure that, in spite of activity reduction of down to 10%, the sensitivity of the sensor is still sufficient for monitoring the respective process, respectively the process medium flowing through.

After termination of the sterilization and after cooling the housing exterior of the housing 102, respectively the environment of the inline sensor arrangement 107, to less than 80° C., preferably less than 60° C. or even less than 40° C., contact between the sensor element 105, respectively the chamber 114, and the interior of the process container 108 is produced, in order to introduce the sensor element 105 aseptically into the process container 108 and so to enable the registering of measured values in a measured medium contained in the process container 108 or flowing through the process container 108. In the present example, the end wall 109 of the housing 102 is embodied sufficiently thinly that it can be mechanically pierced. The end of the sensor element support 104 with the sensor element 105 facing the wall 109 includes a point or edge. The sensor element support 104 is axially movably mounted, for example, by means of a ballpoint pen mechanism, wherein the sensor element support 104 is movable relatively to the wall 109 sufficiently far in the axial direction that the end edge or point of the sensor element support 104 pierces the wall 109 and moves sufficiently beyond the end of the housing 102 into the process container 108 that the sensor element 105 protrudes inwardly into the process container 108. In this position, the inline sensor arrangement 107 can serve to monitor the measured variable to be registered for a process medium contained in the process container 108 or flowing therethrough.

Already in the manufacture of the inline sensor arrangement 107, in the case of which the sensor element 105 on the sensor element support 104 is sealed in the housing 102, respectively in the chamber 114 formed in the housing 102, the housing 102, respectively the chamber 114, can first be evacuated and then the housing interior with the sensor element 105 sterilized, e.g. by gamma radiation. A user need then, for placing the inline sensor arrangement 107 in service, only integrate the inline sensor arrangement 107 into a wall of a process container and perform the heat sterilization.

According to the example of an embodiment described here, the thermal decoupling of the sensor element 105 from the housing exterior of the inline sensor arrangement 107 exposed to the sterilization medium, here superheated steam, serves to avoid destruction of the biological detection elements during a heat sterilization of the process container 108 with the inline sensor arrangement 107 integrated therein. Advantageously in variations of the inline sensor arrangement 107 described here, supplementally to this thermal decoupling, measures can be applied, in order to keep the relative humidity within the chamber 114 below a value of 77% or less during the heat sterilization. As explained above, in this way, a denaturing of the detection elements can likewise be prevented. Optional measures for preventing a too high relative humidity in the chamber 114 include, for example, the application of materials with small water vapor permeability for the components surrounding the chamber 114, such as described based on the example of an embodiment illustrated in FIG. 1, the adding of a drying means into the chamber 114 during the manufacture of the inline sensor arrangement 107 or the supplying of a waterfree or low humidity fluid, especially pure nitrogen or air with a water content of less than 50 ppmv $H_2O$, or even less than 5 ppmv $H_2O$ via a sterile filter, which the fluid passes through, e.g. via the connector 101, before entry into the chamber 114.

Figure 3:
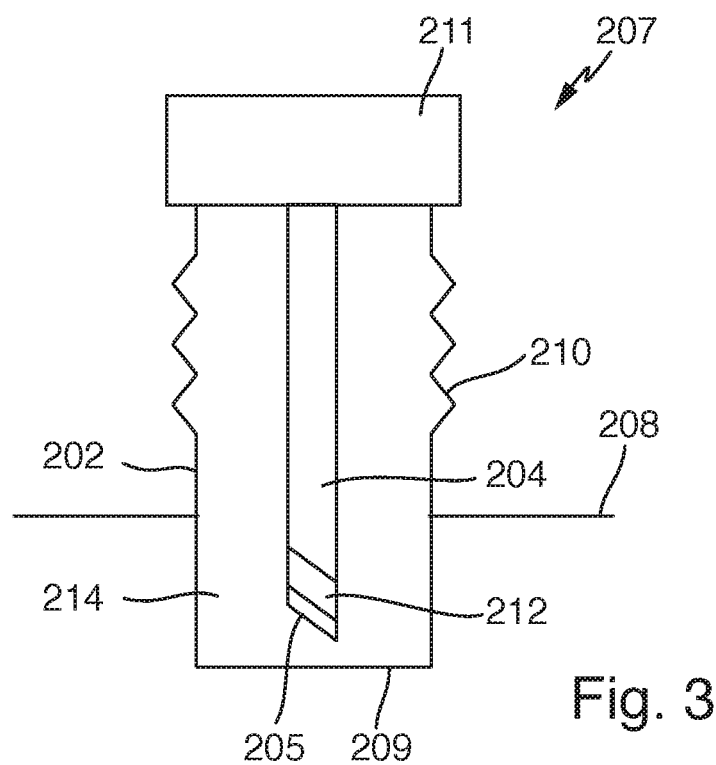
FIG. 3 shows a schematic representation of a third example of an embodiment of an inline sensor arrangement integrated into the wall of a process container.

FIG. 3 shows schematically a further example of an embodiment of an inline sensor arrangement 207. This inline sensor arrangement 207 includes a sensor having a sensor support 204, on which an analyte sensitive, sensor element 205 is arranged. This can be embodied in manner equal to that of the sensor, respectively the sensor element support 4 and the sensor element 5, of the inline sensor arrangement 7 described above based on FIG. 1. The sensor element 205 is connected via electrical lines, which can be led within a channel formed in the sensor element support 204, with a measurement circuit, which is arranged in an electronics housing 211. The measurement circuit is embodied to produce a measurement signal dependent on the measured variable registered by the sensor element 205 and to output such to a superordinated unit, e.g. a measurement transmitter. The measurement circuit and the superordinated unit can be connected with one another, for example, via a cable or via a radio connection.

The sensor support 204 with the sensor element 205 is connected in the example of an embodiment shown here rigidly with the electronics housing 211. The electronics housing 211 seals the rear end of an essentially cylindrical housing 202, which surrounds the sensor element support 204 with the sensor element 205 and encloses such gas tightly in a chamber 214. Housing 202 is secured by means of a connector apparatus (not illustrated in greater detail) sealedly in a wall of a process container 208, so that the inline sensor arrangement 207 is integrated into the process container 208. Housing 202 seals the sensor element 205 and the sensor element support 204, by their being enclosed in the chamber 214, completely from the process container 208.

Housing 202 includes a wall region embodied as a bellows 210. Bellows 210 can be compressed in such a manner that the difference between the length of the housing 202 (measured in the axial direction) in the relaxed state of the bellows 210 and the length of the housing 202 in the case of maximum compression of the bellows 210 is greater than the separation between the end wall 209 of the housing 202 facing the process container 208 and the sensor element 205, wherein this separation corresponds to a distance extending in the axial direction between the wall 209 and the point of the sensor element 205 arranged farthest removed from the wall 209. The inline sensor arrangement 207 can supplementally have locking elements (not shown in FIG. 3), which secure the bellows 210 in the compressed state.

Wall 209 can be embodied as a membrane or as a relatively thin, wall section. For example, the wall can be a humidity impermeable film, which has at least one metal ply, which has a low water vapor permeability. The end of the sensor element support 204 facing the wall 209 can have an edge or point suitable for piercing the wall 209 for opening the chamber 214 to the process container 208 by establishing a connection between the interior of the housing 202 and the interior of the process container 208.

Serving for thermally decoupling of the sensor element 205 from the housing exterior of the housing 202 is a Peltier element 212, which is flushly in contact with the rear side of the sensor element 205 facing the sensor element support 204. Electrical connections of the Peltier element 212 can be contacted via lines extending through the channel formed in the sensor element support 204. The Peltier element 212 can then be operated by means of the measurement circuit. For heat removal, the Peltier element 212 can be in contact with a heat sink. This can comprise a fluid-cooling unit formed within the sensor element support 204. For example, the fluid-cooling unit can have a cooling circuit formed as a duct structure within the sensor element support 204 and flowed through by fluid.

In alternative embodiments, it is also possible actively alone to cool the sensor element 205 by means of a fluid-cooling system. This can be supported within the sensor and/or formed within the interior of the housing 202 or within the wall of the housing 202. In another alternative embodiment, the heat sink interacting with the Peltier element 212 can be formed of a material with high heat capacity and/or large surface area, for example, in the form of cooling fins or ribs.

Before or after integrating the inline sensor arrangement 207 into a wall of the process container 208, the interior of the housing 202 with the therein sensor element 205 and the sensor element support 204 located in the chamber 214 can be sterilized by means of irradiation with gamma radiation.

In the case of start-up of the process container 208 and the inline sensor arrangement 207, a superheated steam sterilization can be performed in the form of an SIP method with the inline sensor arrangement 207 integrated into the wall of the process container 208. At the same time, an active cooling of the sensor element 205 by means of the Peltier element 212 occurs for thermal decoupling of the sensor element 205 from the housing exterior, i.e. the outwardly directed wall surface of the housing 202, exposed to the superheated steam. Due to the action of the hot steam on the housing outer surface of the housing 202, such is heated to temperatures up to 120° C. At the same time, the thermally decoupled sensor element 205 heats at most up to 80° C., preferably less than 40° C., so that the functionality of the sensor element 205 and therewith of the sensor remains.

After termination of the sterilization, especially after the temperature in the process container 208 has dropped to less than 60° C., preferably less than 40° C., the cooling of the sensor element 205 can be ended. For contacting the sensor element 205 with the interior of the process container 208, respectively with a process medium contained in the process container 208, an axially directed force on the electronics housing 211 can move the sensor element support 204 with the sensor element 205 arranged thereon toward the end wall 209 of the housing 202. In such case, the bellows 211 is compressed. With the terminal edge or point of the sensor element support 204, in this way, the wall 209 can be pierced and the sensor element 205 brought aseptically into contact with the interior of the process container 208. As above described, the bellows 210 is so embodied that upon complete collapse of the bellows 210 the sensor element 205 protrudes out past the length of the housing 202, so that the sensor element 205 is in contact with the interior of the process container 208 and, in contact with a process medium located therein, can register measured values of the measured variable.

Due to the thermal decoupling of the sensor element 205 during the hot steam sterilization, a degrading of the functionality of the sensor element 205 is effectively prevented, even when this biological detection element comprises denaturable enzymes or proteins. Additionally or alternatively, the inline sensor arrangement 207 can be embodied in such a manner that during the hot steam sterilization the relative humidity within the chamber 214 remains below 77%. For this, the measures already described above in connection with the examples of embodiments in FIGS. 1 and 2 are suitable.

Figure 4:
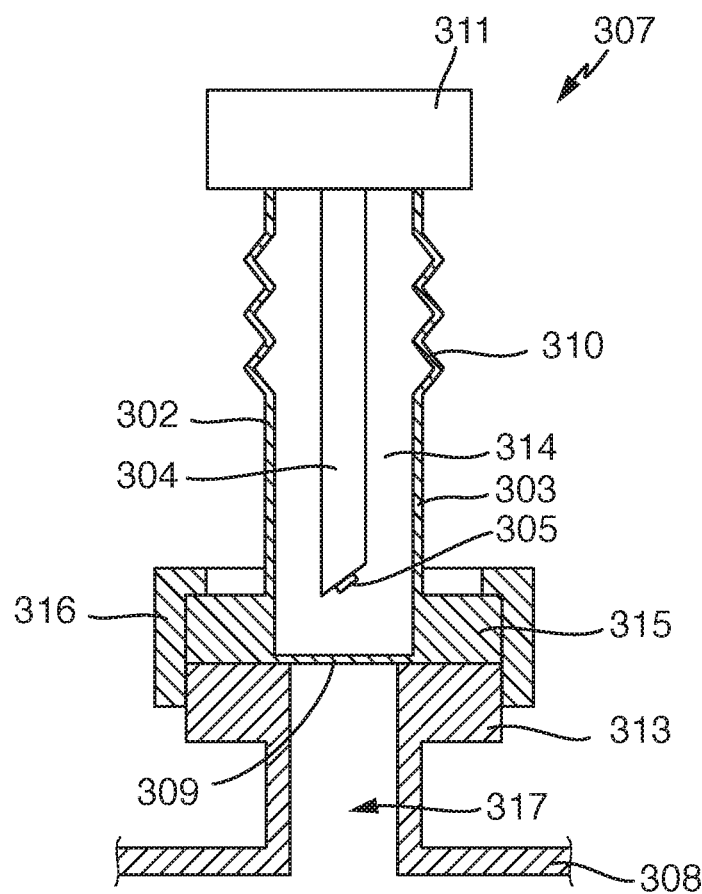
FIG. 4 shows a schematic representation of a process connection of an inline sensor arrangement, which is connected with a connection of a process container.

FIG. 4 shows a further example of an embodiment of an inline sensor arrangement 307, in the case of which a thermal decoupling of a sensor element 305 from a housing exterior of the inline sensor arrangement 307 in contact with the interior of a process container 308 is achieved by spacing the sensor element from the process container 308.

The inline sensor arrangement 307 includes in this example of an embodiment similar to the inline sensor arrangements of the above described examples of embodiments the already mentioned sensor element 305, which can comprise, for example, an electrode modified with biological detection elements for specific interaction with an analyte. The sensor element 305 is arranged on a rod-shaped sensor element support 304. Sensor element 305 and sensor element support 304 are surrounded by a housing 302, which includes a tubular shaft 303, which is sealed at an end facing the process container 308 by an end wall 309. At its other end, the tubular shaft 303 transitions into a bellows 310. Housing 302 is sealed at its end lying opposite wall 309, for example, by means of a potting material (not shown), so that the housing 302 includes a gas tightly closed chamber 314, in which the sensor element support 304 and the sensor element 308 are enclosed.

The inline sensor arrangement 307 includes, moreover, an electronics housing 311, in which a measurement circuit is accommodated, which is connected with the sensor element 305, in order to produce and to output electrical measurement signals, which are correlated with the measured variable registered by the sensor element 305. The measurement circuit can be embodied in the manner of the measuring circuits of the examples of embodiments described above based on FIGS. 1 to 3.

Housing 302 includes on its end associated with the process container 308 a process connection 315, which comprises a flange in the present example. Process connection 315 is connected with a complementary container connection 313 of the process container 308, for example, by means of a securement unit 316, e.g. a coupling nut. Process connection 315 and the housing 302 are connected with one another in the present example in such a manner that the end wall 309 of the housing 302 lies in a plane with the area of the process connection 315 abutting against the container connection 313. In this way, only the end wall 309 comes in contact with the superheated steam in the case of a heat sterilization of the process container 308 by introducing a sterilization medium into the process container 308, not, however, the tubular side wall 303 of the housing 302 or other components of the inline sensor arrangement 307 surrounding the chamber 314.

Generally formulated, this is achieved by the fact that the container connection 313, i.e. the pipe applied on the container and the container flange connected therewith, surrounds, communicating with the interior 306 of the process container 308, a connector space 317, which is sealed on its end facing away from the process container 308 by the wall 309. In this way, it is assured that a sterilization medium entering into the process container 308 comes in contact only with the wall 309, not, however, with the remaining components the inline sensor arrangement 307 in contact with the chamber 314. The process connection 315 is thus connected with the housing 302 of the inline sensor arrangement 307 in such a manner that the sensor element 305 is arranged at the end of the housing wall facing away from the process container 308 and, thus, outside of the connection space 317, when the process connection 315 and the container connection 313 are connected with one another. In such an arrangement, the sensor element 305 arranged axially spaced from the wall 309 is heated less strongly than in the case of an arrangement such as shown, for example, in FIG. 1, in the case of which also the side wall 3 of the housing 2, in the case of a heat sterilization of the process container 8, comes in direct contact with a sterilization medium used for such.

The bringing of the inline sensor arrangement into service and the aseptic contacting of the sensor element 305 with a measured medium contained in the process container 308 can, moreover, occur in the same way as described for the inline sensor arrangement 207 shown in FIG. 3.

Other variations and embodiments of the inline sensor arrangement of the present disclosure can be used. For example, the housing surrounding the sensor element support and the sensor element and during the sterilization of the process container isolating from the interior of the process container can also be so embodied that the establishing of a connection between the sensor element and the inner space of the process container occurs reversibly. For this, the housing wall can include, for example, an opening, which is reversibly closable by means of a lid or cap, in order to partition off the sensor element from the process container, and which can be opened, when a connection between the sensor element and the interior of the process container is to be produced. The housing can also be embodied by a treatment chamber of an immersion or retractable assembly or a lock system, which is embodied in such a manner that the sensor element with the sensor element support can be run in for measuring in the process container or run out from the process container into a chamber sealed from the process container. The chamber and/or the sensor element can, in this case, include means for thermal decoupling of the sensor element from the external, i.e. outwardly facing, wall surface of the chamber, respectively of the housing, in contact with the interior of the process container. In all these embodiments, a multiple application of the housing for the aseptic contacting of a sensor element, especially a heat and/or humidity sensitive sensor element, with a measured medium contained in an earlier heat sterilized process container is possible without removal of the entire inline sensor arrangement, i.e. the same housing can remain in the wall of the process container for a number of production runs with sterilization of the process container being interspersed between the individual batches. It is, in such case, especially possible, that the housing is integrated permanently into the process container, while the sensor element support and the thereon arranged sensor element can be replaced with equally-constructed, other sensor element supports and sensor elements arranged thereon.

The invention claimed is:

1. A method for bringing an inline sensor arrangement into service for registering measured values of a measured variable representing an analyte content of a measured medium, the method comprising:
    providing an inline sensor arrangement including a sensor structured to produce and to output a measurement signal correlated with a measured variable representing an analyte content of a measured medium, wherein the sensor has at least one sterile sensor element configured to contact the measured medium and a housing that surrounds and encloses the sensor element in a chamber sealed from an environment of the housing;
    performing a heat sterilization of at least one part of the inline sensor arrangement including a housing exterior of the housing;
    irreversibly opening the housing to an interior of the container in a sterilized region of the housing exterior of the housing after terminating the heat sterilization; and
    bringing the sensor element into contact with the measured medium.

2. The method of claim 1, wherein the opening of the housing and the bringing of the sensor element into contact with the measured medium occurs aseptically.

3. The method of claim 1, the method further comprising sealedly integrating the inline sensor arrangement into a wall of a process container before the performing of the heat sterilization, wherein the heat sterilization of the inline sensor arrangement is performed simultaneously with a heat sterilization of the process container, and wherein the housing is opened to the process container after termination of the heat sterilization.

4. The method of claim 3, wherein the process container has a container connection that surrounds a connector space communicating with the process container, and the inline sensor arrangement includes a process connection complementary to the container connection, the method further comprising:
    connecting the container connection with the process connection before the performing of the heat sterilization, wherein the process connection is connected with the housing of the inline sensor arrangement such that the sensor element is arranged on a side outside of the connection space and facing away from the process container when the process connection and the connection of the process container are connected with one another.

5. The method of claim 1, wherein the performing of the heat sterilization of the inline sensor arrangement occurs in an autoclave.

6. The method of claim 1, the method further comprising registering the humidity within the housing as a function of time at least during the performing of the heat sterilization, wherein the inline sensor arrangement includes at least one humidity sensor for registering the humidity within the housing.

7. The method of claim 1, wherein the housing includes a wall formed from one or more housing components sealedly enclosing the chamber and forming a barrier against the diffusion of steam into the chamber, and wherein the wall has an average water vapor permeability of less than 420 $g/m^2 \cdot d$, at a temperature of 110° C., a pressure difference between the chamber and the environment of the housing wall of less than 5 bar, and a difference between the relative humidities in the chamber and the environment of the wall of greater than 67%.

8. The method of claim 7, wherein the wall has an average water vapor permeability of less than 125 $g/m^2 \cdot d$.

9. The method of claim 7, wherein the wall has an average water vapor permeability of less than 15 $g/m^2 \cdot d$.

10. The method of claim 7, wherein the wall has an average water vapor permeability of less than 6 $g/m^2 \cdot d$.

11. The method of claim 1, wherein the at least one sensor element includes at least one biological detection element for the analyte.

12. The method of claim 11, wherein the at least one biological detection element for the analyte is an enzyme that is lyophilizable while maintaining at least 10% of its activity.

13. The method of claim 1, wherein the at least one sensor element is an enzyme based glucose sensor including glucose oxidase.

14. The method of claim 1, wherein the at least one sensor element is thermally decoupled from the environment of a housing exterior of the housing at least during the performing of the heat sterilization.

15. The method of claim 1, wherein the inline sensor arrangement includes at least one temperature sensor, the method further comprising:
    monitoring a temperature of the at least one sensor element during the heat sterilization using the at least one temperature sensor.

16. The method of claim 1, wherein the chamber contains silica gel or zeolite.

17. The method of claim 1, wherein a relative humidity within the housing does not exceed 23%.

18. The method of claim 1, wherein a relative humidity within the housing does not exceed 3%.

19. The method of claim 1, wherein a relative humidity within the housing does not exceed 1%.

20. A method for bringing an inline sensor arrangement into service for registering measured values of a measured variable representing an analyte content of a measured medium, the method comprising:

provparams an inline sensor arrangement including a sensor structured to produce and to output a measurement signal correlated with a measured variable representing an analyte content of a measured medium, wherein the sensor has at least one sterile sensor element configured to contact the measured medium and a housing that surrounds and encloses the sensor element in a chamber sealed from an environment of the housing;

performing a heat sterilization of at least one part of the inline sensor arrangement including a housing exterior of the housing;

before performing the heat sterilization, cooling the inline sensor arrangement to less than 8° C.;

opening the housing after terminating the heat sterilization; and bringing the sensor element into contact with the measured medium.

21. The method of claim 20, the inline sensor arrangement is cooled to less than −13° C.

22. The method of claim 20, the inline sensor arrangement is cooled to less than −20° C.

* * * * *